US008891819B2

(12) United States Patent
Kaneda et al.

(10) Patent No.: US 8,891,819 B2
(45) Date of Patent: Nov. 18, 2014

(54) LINE-OF-SIGHT DETECTION APPARATUS AND METHOD THEREOF

(75) Inventors: Yuji Kaneda, Kawasaki (JP); Masakazu Matsugu, Yokohama (JP); Katsuhiko Mori, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 201 days.

(21) Appl. No.: 13/192,923

(22) Filed: Jul. 28, 2011

(65) Prior Publication Data

US 2012/0189160 A1  Jul. 26, 2012

(30) Foreign Application Priority Data

Aug. 3, 2010  (JP) ................. 2010-174730

(51) Int. Cl.
*G06K 9/46* (2006.01)
*G06T 7/00* (2006.01)
*G06K 9/00* (2006.01)
*A61B 3/113* (2006.01)

(52) U.S. Cl.
CPC ............... *A61B 3/113* (2013.01); *G06T 7/0042* (2013.01); *G06K 9/00604* (2013.01); *G06T 2207/30201* (2013.01)
USPC .......... 382/103; 345/158; 348/222.1; 348/77; 351/209

(58) Field of Classification Search
None
See application file for complete search history.

(56) References Cited

U.S. PATENT DOCUMENTS 7,246,904 B2 * 7/2007 Knaan et al. ................... 351/209
8,295,556 B2 * 10/2012 Ohtani et al. ................. 382/118
2004/0174496 A1 * 9/2004 Ji et al. ......................... 351/209
2005/0175218 A1 * 8/2005 Vertegaal et al. ............. 382/103
2005/0200806 A1 * 9/2005 Knaan et al. .................. 351/169
2009/0060291 A1 * 3/2009 Ohtani et al. .................. 382/118
2010/0073503 A1 * 3/2010 Tanaka et al. ............... 348/222.1
2011/0249868 A1 * 10/2011 Tsukizawa et al. ........... 382/103
2012/0224032 A1 * 9/2012 Takiguchi ....................... 348/47
2013/0241955 A1 * 9/2013 Tamaru ........................ 345/633

FOREIGN PATENT DOCUMENTS

| JP | 2003-256852 A | 9/2003 |
| JP | 2007-265367 A | 10/2007 |
| JP | 2008210239 A | 9/2008 |
| JP | 2008282153 A | 11/2008 |
| WO | 2008007781 A1 | 1/2008 |

OTHER PUBLICATIONS

P. Viola, M. Jones, "Rapid Object Detection using a Boosted Cascade of Simple Features", in Proc. of CVPR, vol. 1, pp. 511-518, Dec. 2001.

* cited by examiner

*Primary Examiner* — Tsung-Yin Tsai
(74) *Attorney, Agent, or Firm* — Canon U.S.A., Inc. IP Division

(57) ABSTRACT

A line-of-sight detection apparatus includes a detection unit configured to detect a face from image data, a first extraction unit configured to extract a feature amount corresponding to a direction of the face from the image data, a calculation unit configured to calculate a line-of-sight reliability of each of a right eye and a left eye based on the face, a selection unit configured to select an eye according to the line-of-sight reliability, a second extraction unit configured to extract a feature amount of an eye region of the selected eye from the image data, and an estimation unit configured to estimate a line of sight of the face based on the feature amount corresponding to the face direction and the feature amount of the eye region.

9 Claims, 24 Drawing Sheets

FEATURE POINT POSITION

TEMPLATE (2030)

SCAN

2032

MATCHING RESULT (2031)

LINE-OF-SIGHT DETECTION APPARATUS AND METHOD THEREOF

BACKGROUND OF THE INVENTION

1. Field of the Invention

The present invention relates to a technology for estimating the line of sight of a person in an image.

2. Description of the Related Art

Conventionally, a technology for determining the line of sight of a person is known in which a face image including the black and the outer corner of the right and left eyes are used (for example, see Japanese Patent Application Laid-Open No. 2003-256852). However, as illustrated in FIG. 24, this conventional technology estimates only the eye direction $\alpha 1$ but does not consider the face direction $\beta 1$. On the other hand, another technology is known in which the feature points of organs, such as the eye, are detected from the face in the image data and, using the distance between the detected feature points, the line of sight direction is estimated from both the eye direction $\alpha 1$ and the face direction $\beta 1$ (for example, see Japanese Patent Application Laid-Open No. 2007-265367).

However, one of the problems with the conventional technology is a significant decrease in the line-of-sight detection accuracy that may be caused, for example, when the face turns sideways and one of the eyes is hidden or when the eyes are hidden by hair. Another problem is caused by the dominant eye. For example, when a person gazes in a predetermined direction, the right eye appears to look in the predetermined direction but the left eye does not appear to look in the predetermined direction.

SUMMARY OF THE INVENTION

The present invention is directed to a line-of-sight detection apparatus that can accurately detect the line of sight without being affected by hidden eyes or the dominant eye.

According to an aspect of the present invention, a line-of-sight detection apparatus includes a detection unit configured to detect a face from image data, a first extraction unit configured to extract a feature amount corresponding to a direction of the face from the image data, a calculation unit configured to calculate a line-of-sight reliability of each of a right eye and a left eye based on the face, a selection unit configured to select an eye according to the line-of-sight reliability, a second extraction unit configured to extract a feature amount of an eye region of the selected eye from the image data, and an estimation unit configured to estimate a line of sight of the face based on the feature amount corresponding to the face direction and the feature amount of the eye region.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 3 is a diagram illustrating the center position of a face and the center positions of the eye, mouth, and so on.

DESCRIPTION OF THE EMBODIMENTS

Various exemplary embodiments, features, and aspects of the invention will be described in detail below with reference to the drawings.

Figure 1:
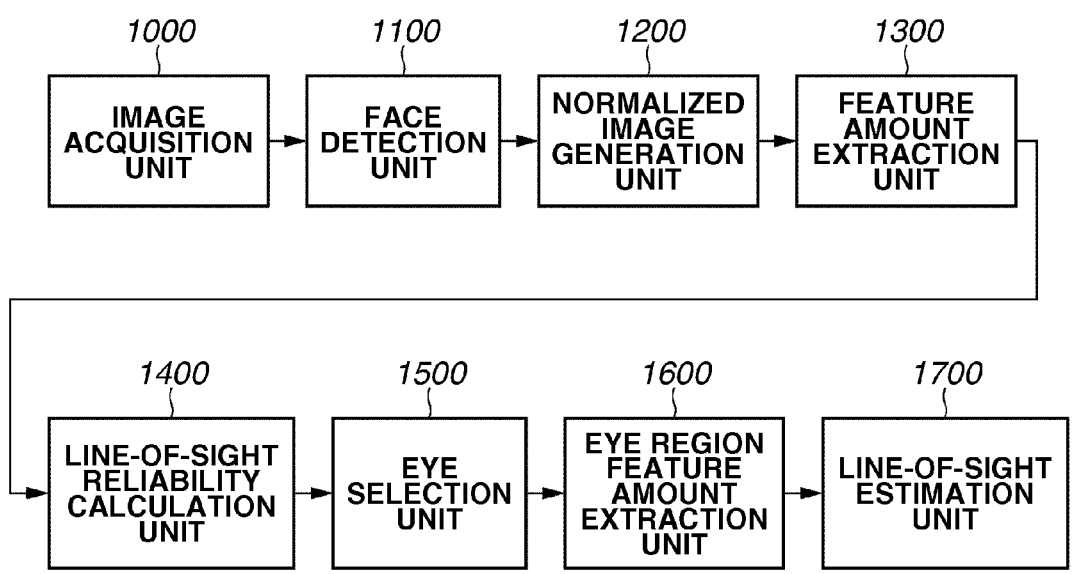
FIG. 1 is a diagram illustrating the functional configuration of a line-of-sight detection apparatus in a first exemplary embodiment of the present invention.

FIG. 1 is a diagram illustrating the functional configuration of a line-of-sight detection apparatus in a first exemplary embodiment of the present invention. The functional configuration illustrated in FIG. 1 is the configuration implemented by downloading the line-of-sight detection program of the present exemplary embodiment into the memory for execution by the central processing unit (CPU).

As illustrated in FIG. 1, the line-of-sight detection apparatus in the present exemplary embodiment includes an image acquisition unit 1000, a face detection unit 1100, a normalized image generation unit 1200, a feature amount extraction unit 1300, a line-of-sight reliability calculation unit 1400, an eye selection unit 1500, an eye region feature amount extraction unit 1600, and a line-of-sight estimation unit 1700. The image acquisition unit 1000 acquires image data from an imaging apparatus. The face detection unit 1100 detects the center position of the face from the image data acquired by the image acquisition unit 1000. In addition, the face detection unit 1100 detects the center positions of the parts of the face such as the eye and the mouth, the more detailed feature points such as the outer corner and the inner corner of the eye, and the positions of organs such as the pupil. The normalized image generation unit 1200 uses the center position of the face and the positions of organs, detected by the face detection unit 1100, to normalize the image data so that the face size is the predetermined size and the face is in the upright direction. From the normalized image data, the normalized image generation unit 1200 generates multiple pieces of image data with different resolutions.

The feature amount extraction unit 1300 uses the image data, generated by the normalized image generation unit 1200, to extract the feature amount corresponding to the face direction. The line-of-sight reliability calculation unit 1400 calculates the reliability of the line of sight based on the center positions and the organ positions detected by the face detection unit 1100. The eye selection unit 1500 selects one of the right eye, left eye, or both eyes as the feature amount extraction object based on the reliability of the line of sight calculated by the line-of-sight reliability calculation unit 1400. The eye region feature amount extraction unit 1600 uses the image data, generated by the normalized image generation unit 1200, to extract the feature amount of the selected eye region. The line-of-sight estimation unit 1700 uses the feature amount corresponding to the face direction extracted by the feature amount extraction unit 1300 and the feature amount of the eye region, extracted by the eye region feature amount extraction unit 1600, to estimate the line of sight direction.

Figure 2:
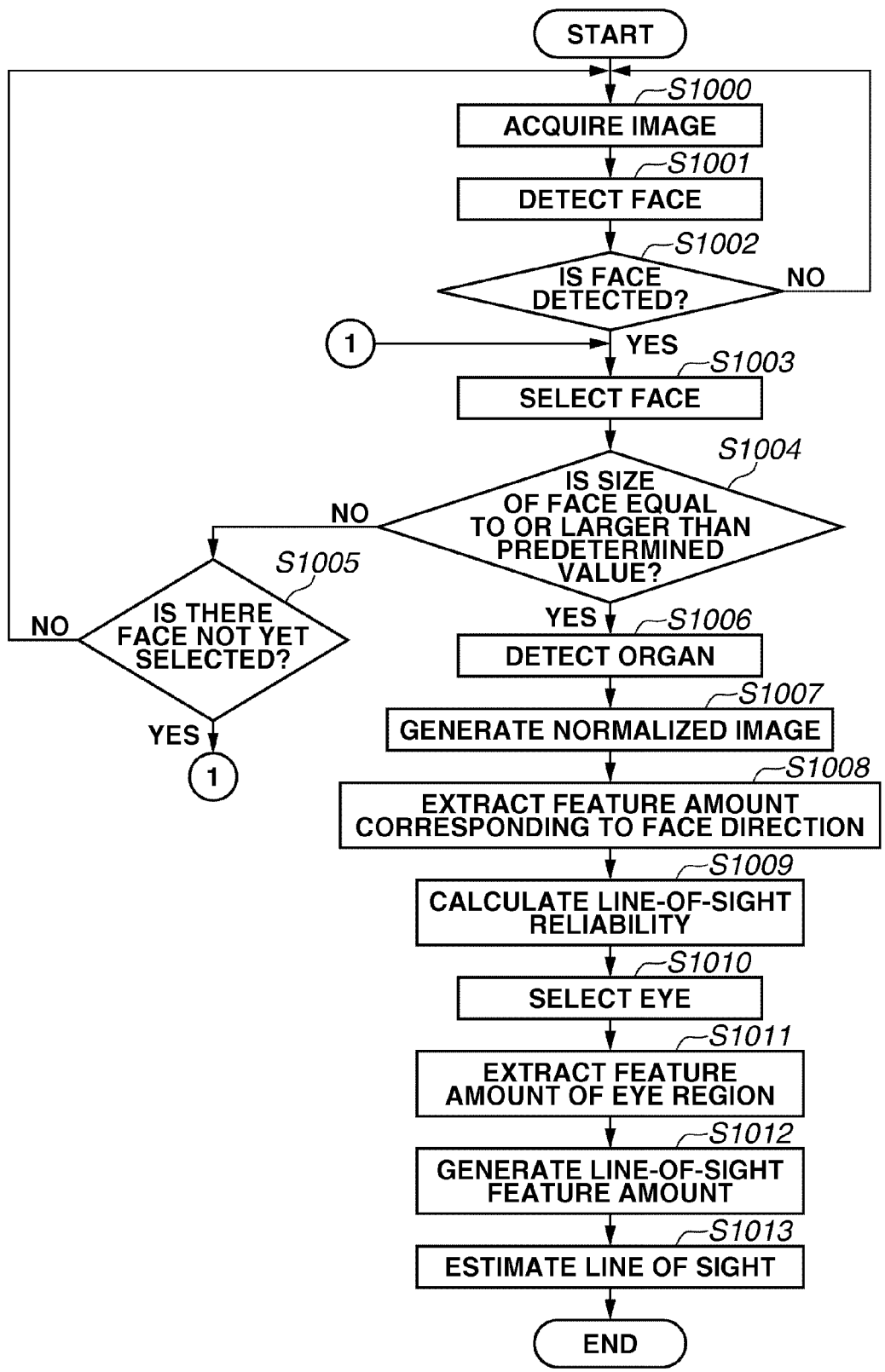
FIG. 2 is a flowchart illustrating a line-of-sight detection method in the first exemplary embodiment.

FIG. 2 is a flowchart illustrating a line-of-sight detection method in the first exemplary embodiment of the present invention. The following describes the line-of-sight detection method in the present exemplary embodiment with reference to FIG. 2.

In step S1000, the image acquisition unit 1000 acquires image data. Image data may be acquired in various ways. For example, image data captured by a digital camera or image data stored in a hard disk drive is acquired.

In step S1001, the face detection unit 1100 determines whether a face is included in the image data acquired in step S1000. Although a human's face is assumed in the present exemplary embodiment, the face of an animal such as a dog or a cat may also be processed. The result obtained in this step is approximately the center position 1032 of the face illustrated in FIG. 3. As the face detection method, the method discussed in the following document may be used.

P. Viola, M. Jones, "Rapid Object Detection using a Boosted Cascade of Simple Features", in Proc. Of CVPR, vol. 1, pp. 511-518, December, 2001

As another method, the face detection system using a neural network is discussed in the following document.

Yusuke Mitarai, Katsuhiko Mori, Masakazu Matsugu, "Robust Face Detection System Based on Convolutional Neural Networks Using Selective Activation of Modules" FIT (Forum in Information Technology), L1-013, 2003

This document also discusses the face detection method that detects the eyes, mouth, and so on and, from their spatial arrangement relation, determines that the image is a face. This detection method sometimes gives the center position of the face as well as the center positions of the eyes, mouth, and so on. The present exemplary embodiment uses this method. Therefore, the face detection processing in step S1001 gives the center position of the face as well as the center positions of the eyes, mouth, and so on.

In step S1002, the face detection unit 1100 determines whether the face is detected. If the face is not detected, the face detection unit 1100 returns processing to step S1000 to acquire another piece of image data. If the face is detected, the face detection unit 1100 advances processing to step S1003 to execute the next step.

In step S1003, the face detection unit 1100 selects one of the faces from those detected in step S1002. In step S1004, the face detection unit 1100 determines whether the size of the face selected in step S1003 is equal to or larger than a predetermined value. For a person with a small face, the amount of information is sometimes too small to detect the line of sight accurately. Therefore, the line-of-sight detection apparatus of the present exemplary embodiment is designed to detect the line of sight only for a face with a predetermined size or larger.

Figure 3:
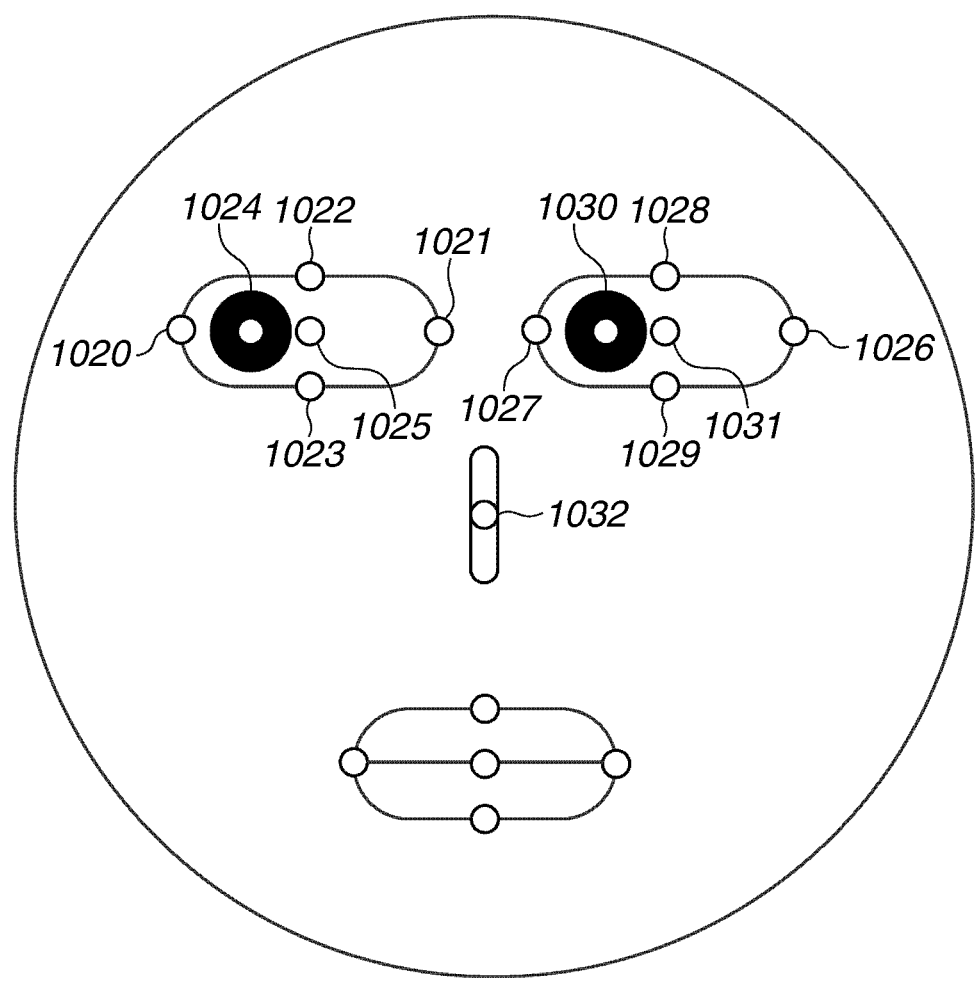

As the size of a face, any measure representing the size of a face may be used; for example, the distance between a right-eye center position 1025 and a left-eye center position 1031 in FIG. 3 or the area of the skin color region may be used. In the present exemplary embodiment, the twice the distance between the right-eye center position 1025 and the left-eye center position 1031 is defined as the size of a face. To search for the right-eye center position 1025 and the left-eye center position 1031, the face detection unit 1100 may set a range in which, with the center position of the face detected in step S1001 as the base, the right and left eyes may be statistically present. Within that range, the face detection unit 1100 uses a predetermined template to search for the right-eye center position 1025 and the left-eye center position 1031.

In step S1004, if the size of the face is determined smaller than the predetermined size, the face detection unit 1100 determines in step S1005 whether there is a face detected in step S1001 but not yet selected. If all faces are selected, the processing returns to step S1000, in which the image acquisition unit 1000 acquires another piece of image data. On the other hand, if there is one or more faces not yet selected, the processing returns to step S1003, in which the face detection unit 1100 selects a face not yet selected.

Figure 7:
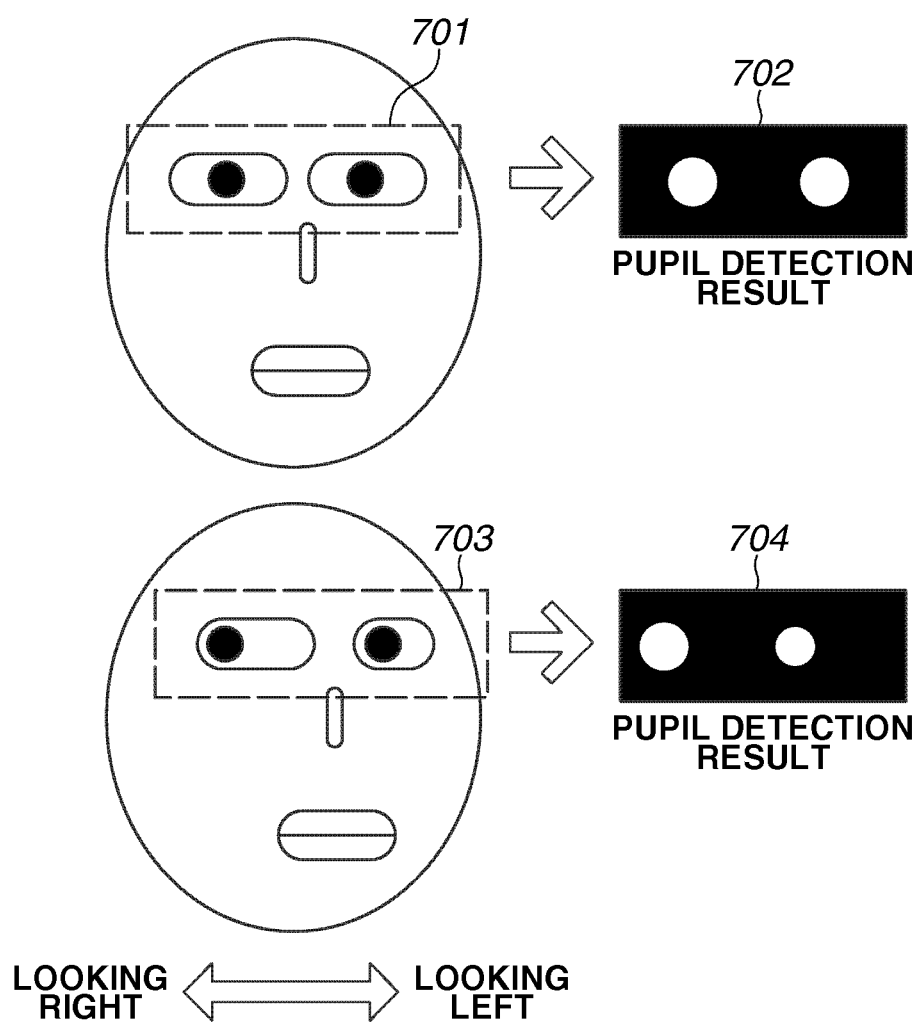
FIG. 7 is a diagram illustrating the processing for detecting the image data of the pupil part from the image data near the eye and for calculating the area of the image data of the pupil part.

On the other hand, if the size of the face is determined equal to or larger than the predetermined value in step S1004, the face detection unit 1100 detects in step S1006 not only the center position 1032 of the face but the feature point positions of the inner corners of the eyes 1021 and 1027 and the outer corners of the eyes 1020 and 1026. In this step, the face detection unit 1100 also detects whether there is a pupil. To detect the feature point positions or to detect whether there is a pupil, the face detection unit 1100 may use various methods; for example, the face detection unit 1100 uses a template prepared in advance, scans the edge, and so on. If the pupil is present, the face detection unit 1100 detects image data 702 and 704 of the pupil from image data 701 and 703 near the eyes, as illustrated in FIG. 7, and calculates the area of the image data of the pupil.

Figure 4:
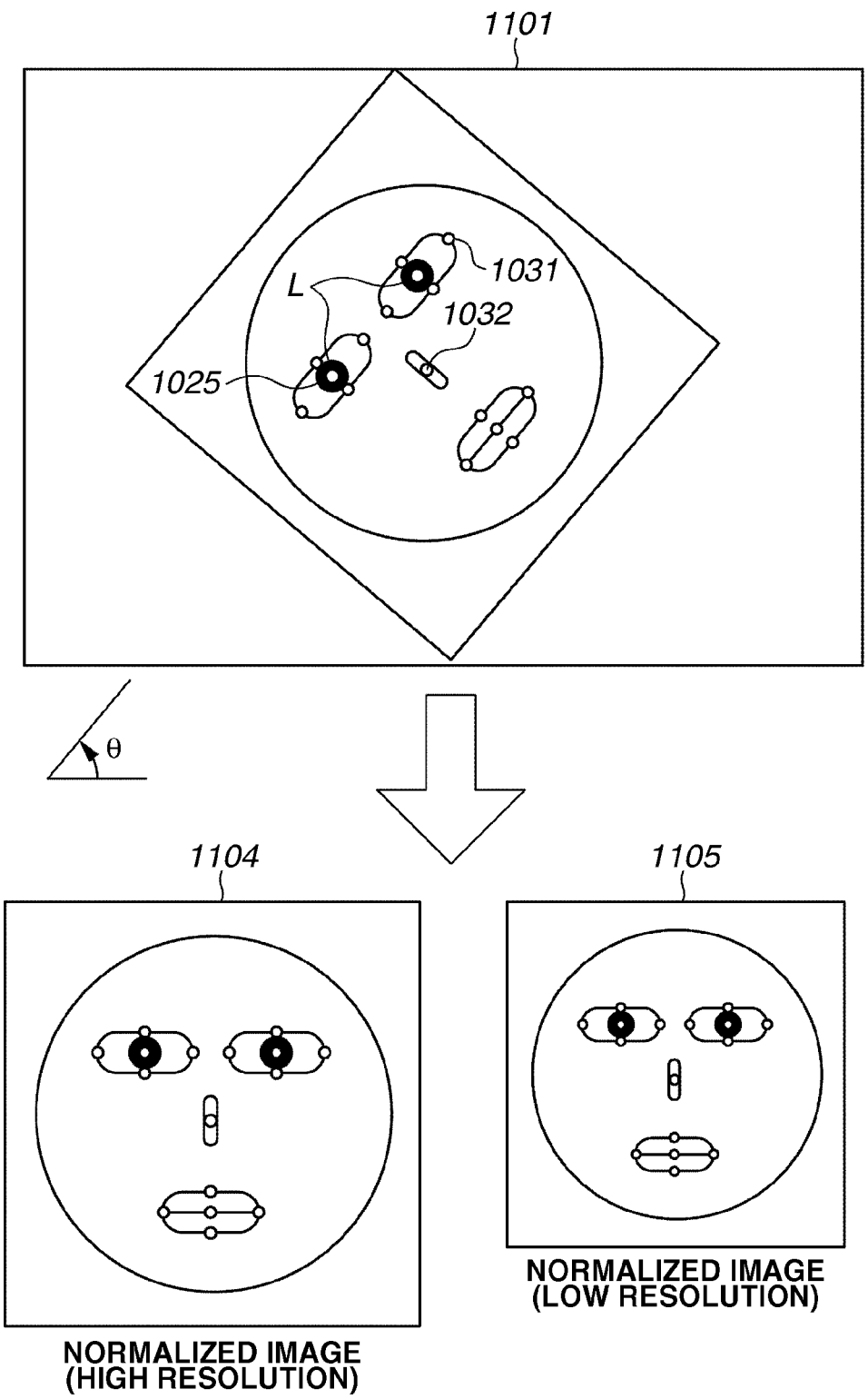
FIG. 4 is a diagram illustrating the normalization processing for image data.

In step S1007, the normalized image generation unit 1200 generates two types of image data 1104 and 1105 as illustrated in FIG. 4. The face in those two types of image data is in the upright direction and has a predetermined size, but the resolution differs between the two types of image data. More specifically, from the right-eye center position 1025 and the left-eye center position 1031 in the image data 1101 before normalization, the normalized image generation unit 1200 calculates the distance L and the angle θ with the horizontal direction as illustrated in FIG. 4. The normalized image generation unit 1200 performs the affine transform so that the distance L=predetermined distance L' and θ=0. There are various enlargement/reduction methods such as the nearest neighbor method and the bilinear method. Although the right-eye center position 1025, left-eye center position 1031, and face center position 1032 are used for normalizing image data in the present exemplary embodiment, other positions may also be used. Note that the two types of image data (hereinafter called normalized image data), normalized in step S1007 and having different resolutions, are each used for extracting the feature amount corresponding to the face direction and the feature amount of the eye region. In addition, to reduce the effect of the illumination, the luminance value may be converted for correcting the contrast.

Instead of generating only two types of normalized image data having different resolutions, multiple pieces of image data (pyramid image) having different resolutions may also be generated in advance so that two types image data may be selected from them. Multiple pieces of image data having different resolutions, if generated in advance in this way, may be used for applications other than line-of-sight detection, for example, for pattern recognition. In addition, it is also possible to generate high-resolution image data first for use in extracting the feature amount of the eye region and, after that, to generate low-resolution image data through the reduction processing for use in extracting the feature amount corresponding to the face direction.

Figure 5A:
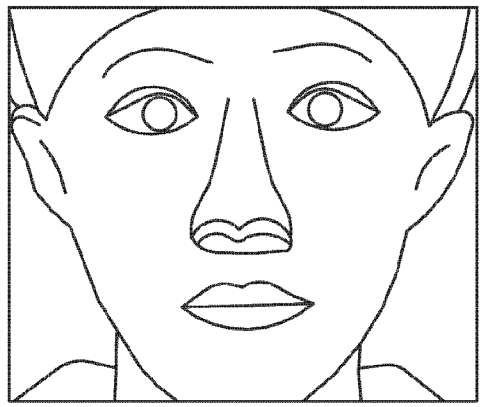
FIGS. 5A-5D are diagrams illustrating the feature amount corresponding to the face direction.
Figure 5B:
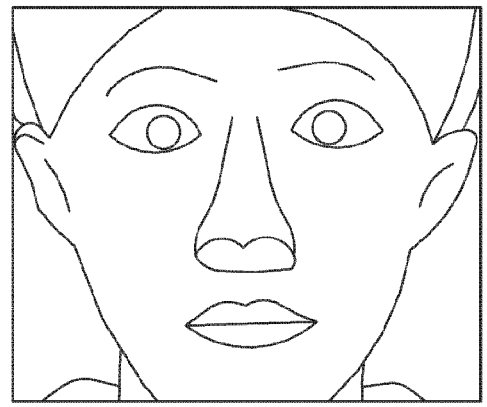
Figure 5C:
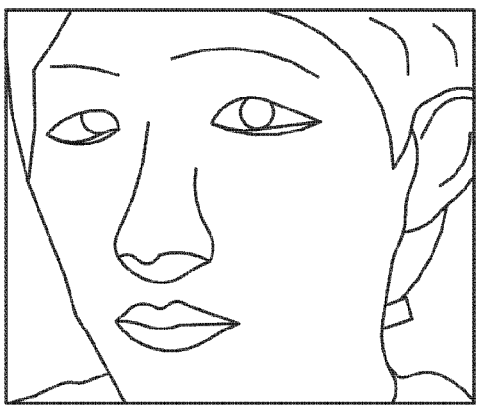
Figure 5D:

In step S1008, the feature amount extraction unit 1300 uses the lower-resolution normalized image data 1105 of the two types of normalized image data, generated in step S1007, to extract the feature amount corresponding to the face direction. In the present exemplary embodiment, the edge feature is used for the feature amount corresponding to the face direction. Usually, the first-order differential or the second-order differential of the pixel values of the image data is usually used to extract the edge feature. In the present exemplary embodiment, the first differential is used to extract the edge feature. FIG. 5A and FIG. 5C illustrate the first-order differential edge image data extracted using the first-order differential in the X direction. FIG. 5B and FIG. 5D illustrate the first-order differential edge image data extracted using the first-order differential in the Y direction. Although the position and the shape of the outline edge of a face are acquired in the present exemplary embodiment, the position and the shape of the ears, nose, and hair may also be used. Therefore, in step S1008, the feature amount extraction unit 1300 generates a feature vector, in which the pixel value configuring the first-order differential edge image data in the X direction and the first-order differential edge image data in the Y direction is one element, as the feature amount of the area. For example, when the first-order differential edge image data in the X direction and the first-order differential edge image data in the Y direction are 30×30, then the 1800-dimensional feature vector is generated. As the feature amount, the luminance or the color may be used instead of the edge. In addition, the frequency, luminance, or their histograms discussed in the document given blow may also be used.

Akiko Suzuki, Tetsuya Takiguchi, Yasuo Ariki "Eye Detection Using PCA Correlation Filter" FIT (Forum in Information Technology), H-015, 2007

M. Bertozzi, A. Broggi, M. Del Rose, M. Felisa, A. Rakotomamonjy and F. Suard, "A Pedestrian Detector Using Histograms of Oriented Gradients and a Support Vector Machine Classifier", IEEE Intelligent Transportation Systems Conference, 2007

Figure 6:
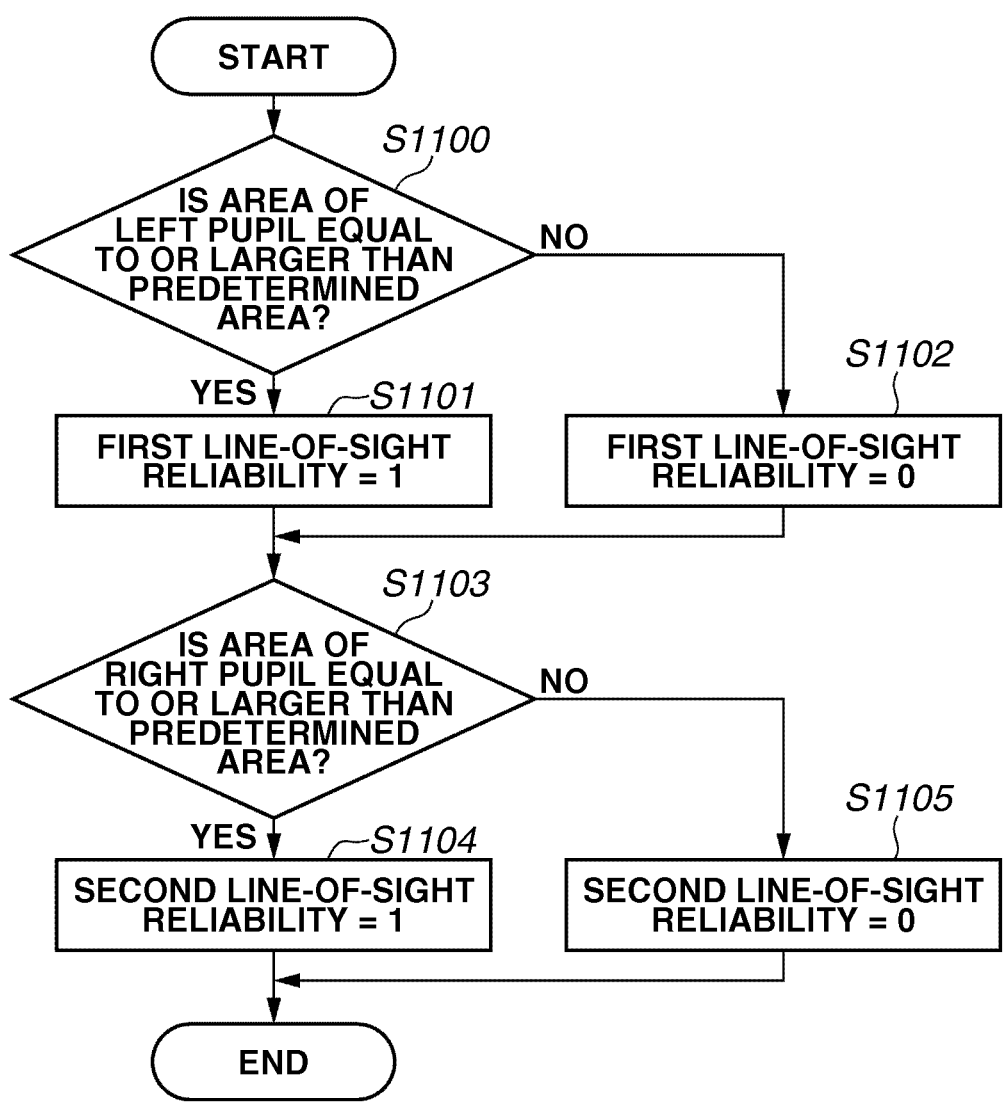
FIG. 6 is a flowchart illustrating the detailed processing procedure for calculating line-of-sight reliability.

Next, in step S1009, the line-of-sight reliability calculation unit 1400 calculates the reliability of the line of sight based on the pupil detection result obtained in step S1006. Here, the reliability is expressed by the eye visibility, which indicates that the higher the value is, the lower the possibility that a problem is generated when the line of sight is used for line-of-sight estimation. FIG. 6 is a flowchart illustrating the detailed processing procedure for calculating the line-of-sight reliability performed in step S1009.

In step S1100, the line-of-sight reliability calculation unit 1400 determines whether the area of the left pupil image data, calculated in step S1006, is equal to or larger than a predetermined area. If the area of the left-pupil image data is equal to or larger than the predetermined area, the line-of-sight reliability calculation unit 1400 sets the first line-of-sight reliability to "1" in step S1101 assuming that the left eye is well visible. On the other hand, if the area of the left-pupil image data is smaller than the predetermined area, the line-of-sight reliability calculation unit 1400 sets the first line-of-sight reliability to "0" in step S1102 assuming that the left eye is not well visible.

In step S1103, the line-of-sight reliability calculation unit 1400 determines whether the area of the right-pupil image data, calculated in step S1006, is equal to or larger than the predetermined area. If the area of the right-pupil image data is equal to or larger than the predetermined area, the line-of-sight reliability calculation unit 1400 sets the second line-of-sight reliability to "1" in step S1104 assuming that the right eye is well visible. On the other hand, if the area of the right-pupil image data is smaller than the predetermined area, the line-of-sight reliability calculation unit 1400 sets the second line-of-sight reliability to "0" in step S1105 assuming that the right eye is not well visible.

As described above, when there is a possibility that the face turns sideways or the eyes are hidden by hair, whether the right/left eye is well visible is represented by the reliability of the line of sight based on the area of the pupil. Instead of the pupil, the area of the eye region including the white may also be used.

In the present exemplary embodiment, the area of the pupil is compared with a threshold and, according to the result, the reliability of the first line-of-sight and the second line-of-sight is set to one of the two values, "0" (unreliable) or "1" (reliable). Instead of comparing the area of the pupil with a threshold, the area of the pupil itself may be set as the first line-of-sight reliability and the second line-of-sight reliability. In addition, the first line-of-sight reliability and the second line-of-sight reliability may be calculated based on the detection result of the feature points of an organ such as the outer corner, inner corner, upper eyelid, or lower eyelid.

Figure 8:
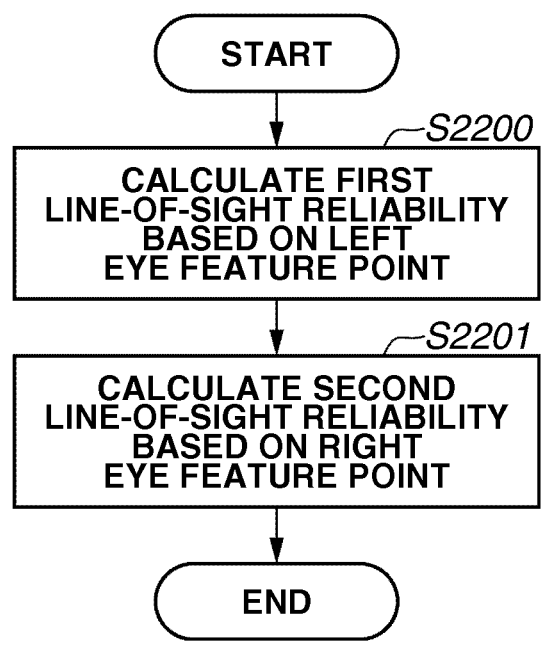
FIG. 8 is a flowchart illustrating the processing for calculating the first line-of-sight reliability and the second line-of-sight reliability.

FIG. 8 is a flowchart illustrating the processing procedure used by the line-of-sight reliability calculation unit 1400 for calculating the reliability of the first line-of-sight and the second line-of-sight based on the spatial arrangement of the feature point detection positions. In step S2200, the line-of-sight reliability calculation unit 1400 calculates the first line-of-sight reliability based on the left eye feature point (outer corner, inner corner, upper eyelid, lower eyelid) detection position. In this case, the Y-coordinate of the outer-corner feature point position is almost equal to the Y-coordinate of the inner-corner feature point position. Similarly, the X-coordinate of the upper-eyelid feature point position is almost equal to the X-coordinate of the lower-eyelid feature point position. The midpoint between the X-coordinate of the outer-corner feature point position and the X-coordinate of the inner corner feature point position is almost equal to the X-coordinate of the upper-eyelid feature point position and to the X-coordinate of the lower-eyelid feature point.

Figure 9:
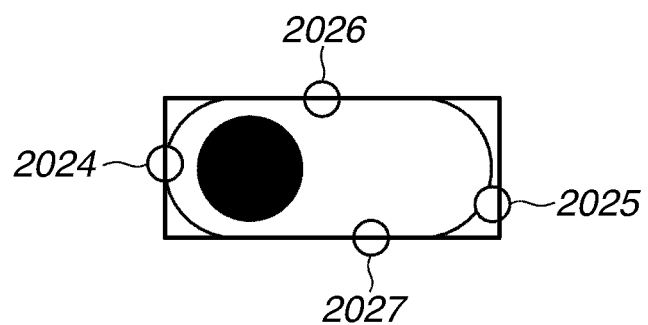
FIG. 9 is a diagram illustrating the feature point positions of the eye.

In the processing illustrated in FIG. 8, the line-of-sight reliability calculation unit 1400 uses the spatial arrangement relation among those feature point positions to set the line-of-sight reliability. More specifically, as illustrated in FIG. 9, if the detected feature point positions—an outer-corner feature point position 2024, an inner-corner feature point position 2025, an upper-eyelid feature point position 2026, and a lower-eyelid feature point position 2027—satisfy all four conditions given below, the line-of-sight reliability calculation unit 1400 sets the line-of-sight reliability to "1". Note that the applicable conditions are not limited to the four conditions given below.

| | |
|---|---|
| Y-coordinate of outer-corner feature point−Y-coordinate of inner-corner feature point<$Th1$ | Condition 1 |
| X-coordinate of upper-eyelid feature point−X-coordinate of lower-eyelid feature point<$Th2$ | Condition 2 |
| (X-coordinate of outer-corner feature point+X-coordinate of inner-corner feature point)/2−X-coordinate of upper-eyelid feature point<$Th3$ | Condition 3 |
| (X-coordinate of outer-corner feature point+X-coordinate of inner-corner feature point)/2−X-coordinate of lower-eyelid feature point<$Th4$ | Condition 4 | where, Th1-Th4 are predetermined thresholds. Instead of comparing with a threshold in each of conditions 1-4, the left-side values of conditions 1-4 may be used as the line-of-sight reliability. In this case, the closer the value is to "0", the higher the reliability is. In step S2201, the line-of-sight reliability calculation unit 1400 calculates the second line-of-sight reliability based on the right-eye feature point (outer corner, inner corner, upper eyelid, and lower eyelid) positions.

Figure 10:
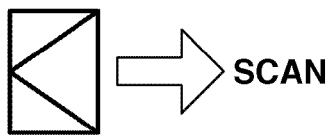
FIG. 10 is a diagram illustrating the matching result between a template for detecting the feature point of the outer corner of the eye and the image data of the eye.
Figure 10:
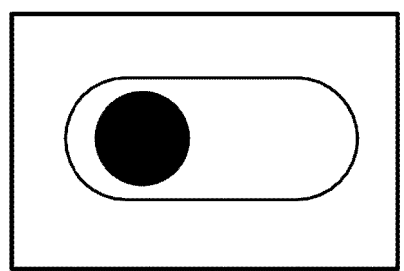
Figure 10:
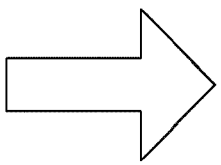
Figure 10:
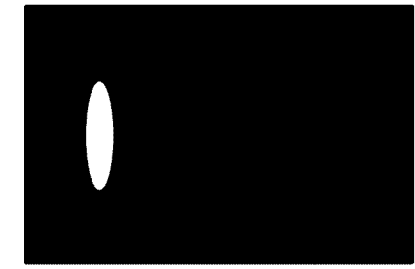

In addition to the spatial arrangement relation among the feature point detection positions of the eyes, the distribution of the feature point detection positions themselves may be used. FIG. 10 is a diagram illustrating a template 2030 for detecting the outer-corner feature point and a matching result 2031 between the template 2030 and eye image data 2032. The white region of the matching result 2031 in FIG. 10 indicates a region that is included in the eye image data 2032 and is more likely to match the template 2030. Therefore, the line-of-sight reliability calculation unit 1400 may calculate the variance and the acutance of the pixel values having a predetermined value or larger in this white region and, based on those values, calculate the line-of-sight reliability.

In addition, the line-of-sight reliability calculation unit 1400 may use the feature amount, corresponding to the face direction extracted in step S1008, to estimate the face direction and calculate the line-of-sight reliability based on the estimated face direction. To estimate the face direction, a face-direction estimation apparatus is needed. In the present exemplary embodiment, a support vector machine (hereinafter called SVM) discussed in the document below is used. Note that the face-direction estimation apparatus usable in the present invention is not limited to the SVM.

V. Vapnik. "Statistical Learning Theory", John Wiley & Sons, 1998

Figure 11:
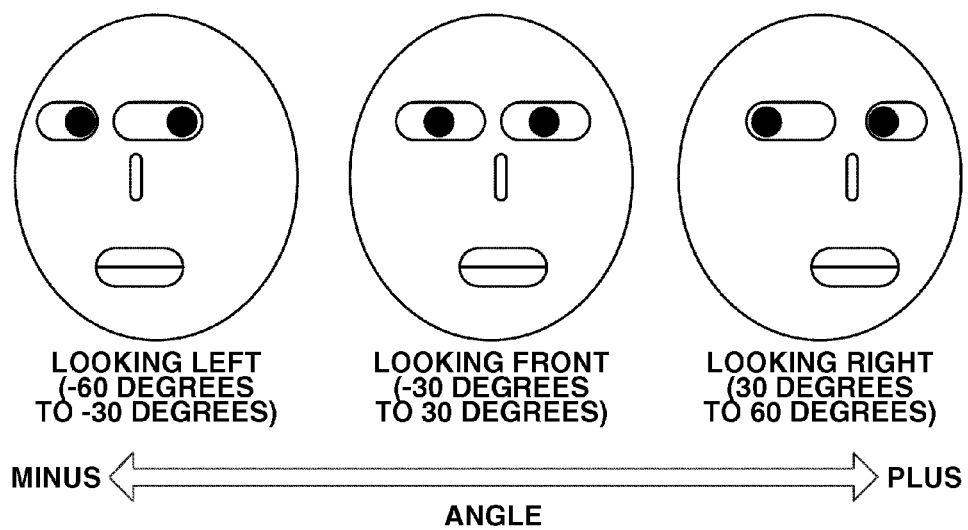
FIG. 11 is a diagram illustrating the processing for calculating the line-of-sight reliability based on the face direction.

For example, as illustrated in FIG. 11, classifiers that classify the face direction into three patterns, looking left (−60 degrees to −30 degrees), looking front (−30 degrees to 30 degrees), and looking right (30 degrees to 60 degrees), are prepared in advance. More specifically, the looking-left classifier determines the looking-left direction as positive data, and others as negative data. Similarly, the looking-front classifier and the looking-right classifier are prepared. The line-of-sight reliability calculation unit 1400 determines the face direction of a person based on the classifier that calculates the highest value among the three classifiers. Although the three face-direction resolutions are used in the present exemplary embodiment, the face direction is not limited to the three. In addition, though the looking-left direction is defined as the range of −60 degrees to −30 degrees, the looking-front direction as the range of −30 degrees to 30 degrees, and the looking-right direction as the range of 30 degrees to 60 degrees, the face direction is not limited to those angles.

Figure 12:
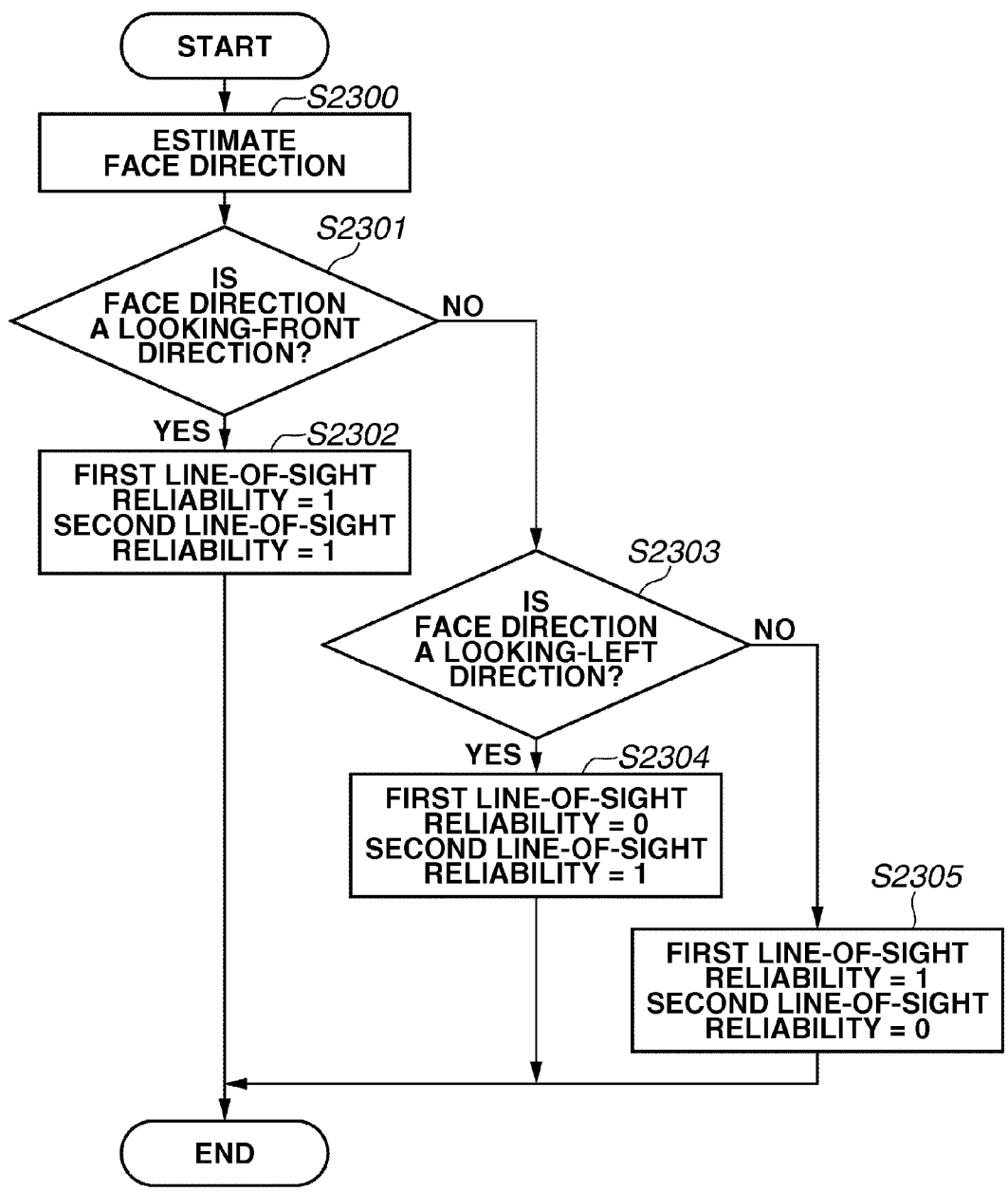
FIG. 12 is a flowchart illustrating the processing for setting line-of-sight reliability.

FIG. 12 is a flowchart illustrating the processing executed by the line-of-sight reliability calculation unit 1400 for setting the line-of-sight reliability based on the face direction estimation result. In step S2300, the line-of-sight reliability calculation unit 1400 uses the feature amount, corresponding to the face direction extracted in step S1008, to estimate the face direction. In step S2301, the line-of-sight reliability calculation unit 1400 determines whether the face direction is the looking-front direction. If the face direction is the looking-front direction, the line-of-sight reliability calculation unit 1400 sets the first line-of-sight reliability to "1", and the second line-of-sight reliability to "1", in step 2302. On the other hand, if the face direction is not the looking-front direction, the line-of-sight reliability calculation unit 1400 determines in step S2303 whether the face direction is the looking-left direction. If the face direction is the looking-left direction, the line-of-sight reliability calculation unit 1400 sets the first line-of-sight reliability to "0", and the second line-of-sight reliability to "1", in step S2304. On the other hand, if the face direction is not the looking-left direction, the line-of-sight reliability calculation unit 1400 sets the first line-of-sight reliability to "1", and the second line-of-sight reliability to "0", in step S2305.

Figure 13:
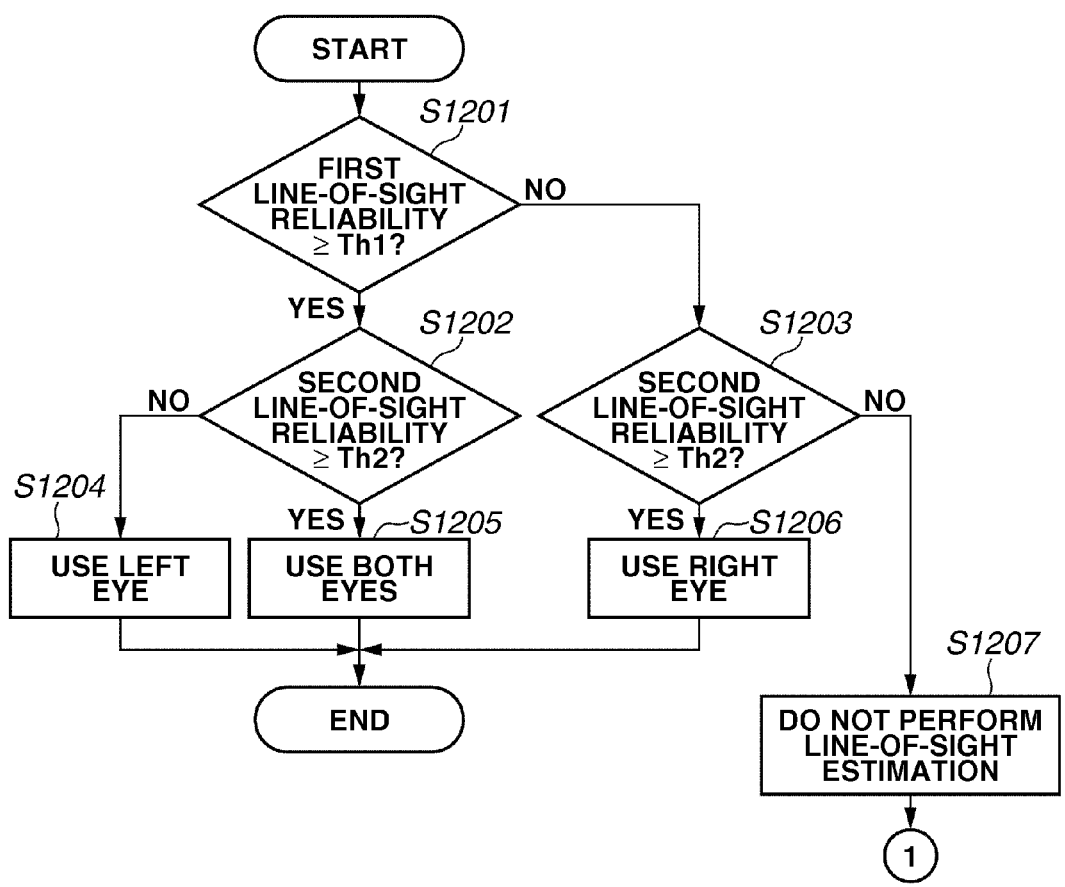
FIG. 13 is a flowchart illustrating the detailed processing procedure for selecting the eye.

In step S1010, the eye selection unit 1500 selects which to use, right eye, left eye, or both eyes, as the feature amount of the eye region based on the first line-of-sight reliability and the second line-of-sight reliability calculated in step S1009. FIG. 13 is a flowchart illustrating the detailed processing of step S1010.

In step S1201, the eye selection unit 1500 determines whether the first line-of-sight reliability is equal to or larger than a predetermined threshold Th1. If the first line-of-sight reliability is equal to or larger than the threshold Th1, the eye selection unit 1500 determines in step S1202 whether the second line-of-sight reliability is equal to or larger than a predetermined threshold Th2. If the second line-of-sight reliability is equal to or larger than Th2, the eye selection unit 1500 determines to use the both eyes as the feature amount of the eye region in step S1205. On the other hand, if the second line-of-sight reliability is smaller than the predetermined threshold Th2, the eye selection unit 1500 determines to use the left eye as the feature amount of the eye region in step S1204.

On the other hand, if it is determined in step S1201 that the first line-of-sight reliability is smaller than the predetermined threshold Th1, the eye selection unit 1500 determines in step S1203 whether the second line-of-sight reliability is equal to or larger than the predetermined threshold Th2. If the second line-of-sight reliability is equal to or larger than the predetermined threshold Th2, the eye selection unit 1500 determines to use the right eye as the feature amount of the eye region in step S1206. On the other hand, if the second line-of-sight reliability is smaller than the predetermined threshold Th2, the eye selection unit 1500 determines in step S1207 that line-of-sight estimation is not performed because the both eyes are not well visible.

If the line-of-sight reliability is represented in one of the two values, "0" or "1", the thresholds Th1 and Th2 are set to "1". In the present exemplary embodiment, the eye selection unit 1500 evaluates the visibility of the left eye and the right eye based on the line-of-sight reliability and, based on the evaluation result, selects the right eye, left eye, or both eyes as the feature amount of the eye region.

In step S1011, the eye region feature amount extraction unit 1600 uses the normalized image data 1104, which is one of two types of normalized image data generated in step S1007 and has a higher resolution, to extract the feature amount of the eye region. More specifically, because the pupil motion is very small, the eye region feature amount extraction unit 1600 uses the higher resolution normalized image data 1104 to detect the small motion accurately. This means that the feature of the entire face region must be extracted to detect the face direction but that only the feature amount of the eye region need be extracted to detect the eye direction. The addition of a feature amount other than that of the eye region may result in an increase in the feature vector dimension with the result that the processing load in the subsequent stages will increase. In addition, a feature amount other than that of the eye region may affect the line-of-sight detection accuracy. Therefore, the feature points are used in the present exemplary embodiment to limit the eye region. In addition, the normalization processing is performed to absorb the difference in the eye size among persons.

Figure 14:
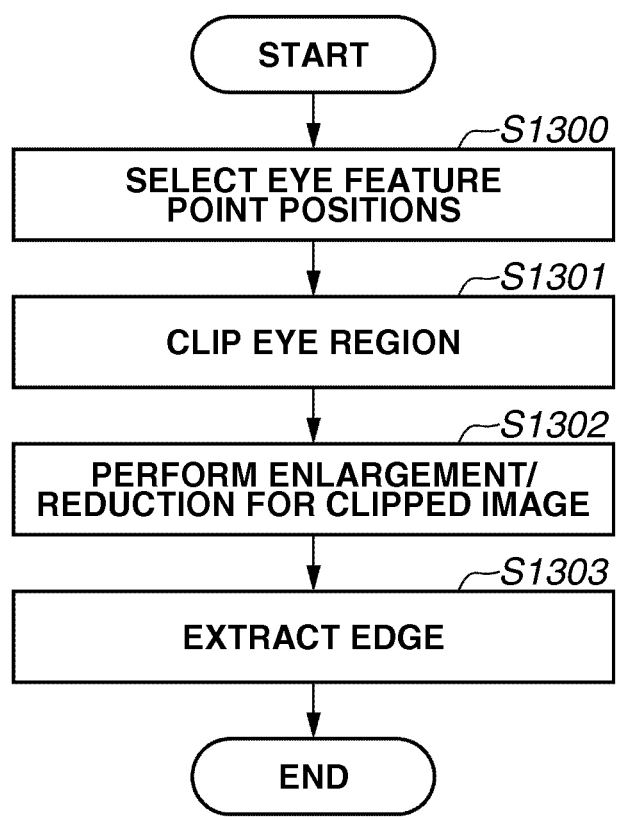
FIG. 14 is a flowchart illustrating the detailed procedure for the feature amount extraction processing for the eye region.

FIG. 14 is a flowchart illustrating the detailed procedure for the feature amount extraction processing for the eye region performed in step S1011 in FIG. 2. In step S1300, the eye region feature amount extraction unit 1600 selects the four feature point positions of the right and left eyes from the feature point positions detected in step S1006. The four feature point positions of the right and left eyes are outer corner feature point positions 1020 and 1026, inner corner feature point positions 1021 and 1027, upper eyelid feature point positions 1022 and 1028, and lower eyelid feature point points 1023 and 1029 illustrated in FIG. 3.

Figure 15:
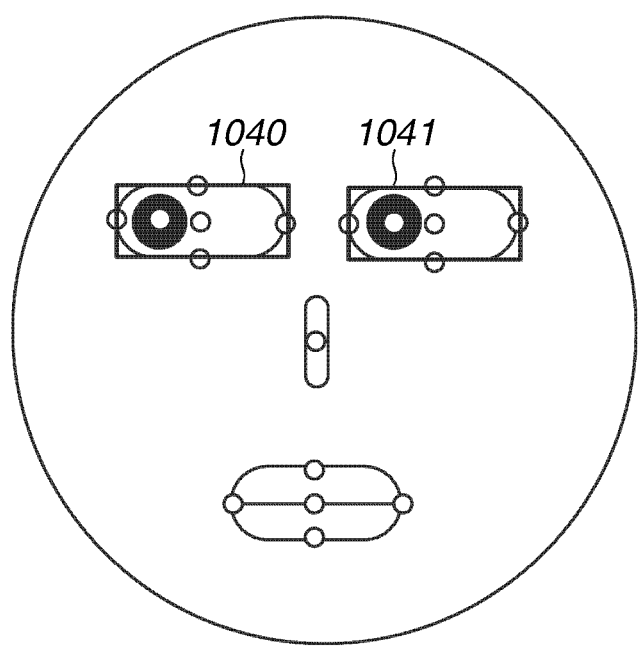
FIG. 15 is a diagram illustrating the processing for clipping the image data of the left eye region and the image data of the right eye region.

In step S1301, the eye region feature amount extraction unit 1600 clips the image data of the eye region based on the eye selection result obtained in step S1010. More specifically, if the right eye is selected in step S1010, the eye region feature amount extraction unit 1600 uses the four feature point positions 1020, 1021, 1022, and 1023 of the right eye to clip the image data of a right eye region 1040 illustrated in FIG. 15. On the other hand, if the left eye is selected in step S1010, the eye region feature amount extraction unit 1600 uses the four feature point positions 1026, 1027, 1028, and 1029 of the left eye to clip the image data of a left eye region 1041 illustrated in FIG. 15. If both eyes are selected in step S1010, the eye region feature amount extraction unit 1600 uses the four feature point positions 1020, 1021, 1022, and 1023 of the right eye and the four feature point positions 1026, 1027, 1028, and 1029 of the left eye to clip the image data of the right eye region 1040 and the left eye region 1041 illustrated in FIG. 15.

Figure 16:
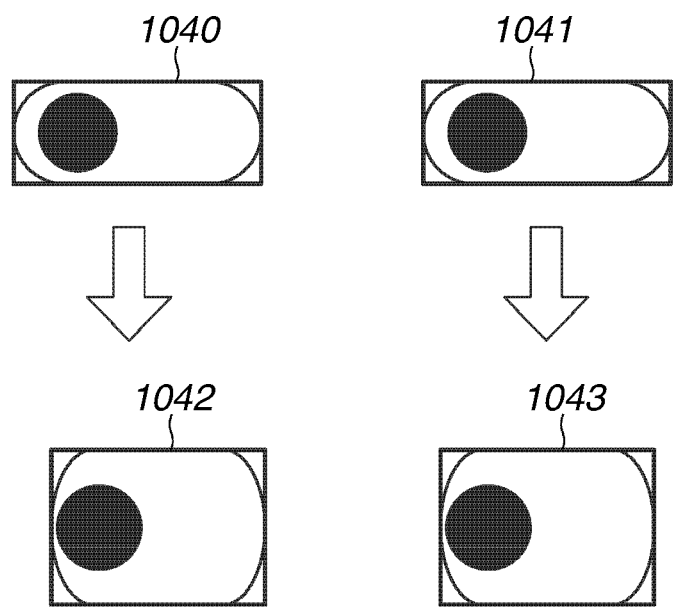
FIG. 16 is a diagram illustrating the normalization processing for the image data of the eye region.
Figure 17:
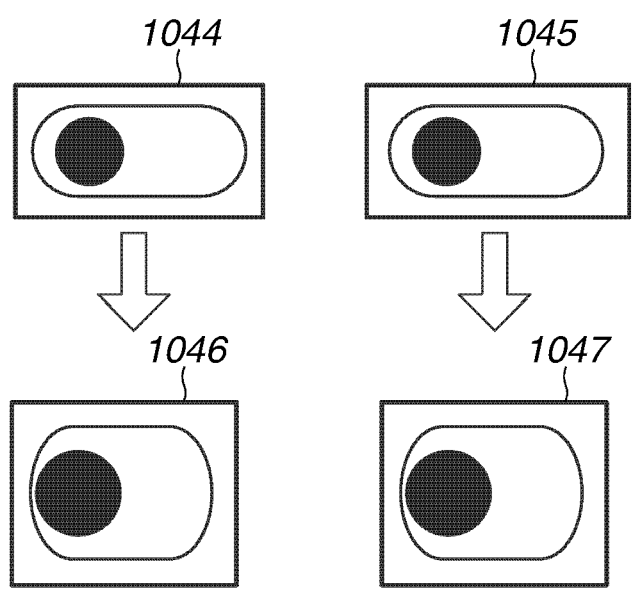
FIG. 17 is a diagram illustrating the normalization processing for the image data of the eye region.

In step S1302, the eye region feature amount extraction unit 1600 performs enlargement/reduction processing for each of the image data 1040 and 1041, clipped in step S1301, as illustrated in FIG. 16 so that the width and the height of the image data become predetermined sizes 1042 and 1043. This processing absorbs the difference in eye size among the individuals. Note that, in clipping the image data of the left eye and the right eye in step S1301, the image data including the eye outlines may be clipped as indicated by areas 1044 and 1045 in FIG. 17 instead of clipping the image data including the feature point positions as illustrated in FIG. 16. In this case, the eye region feature amount extraction unit 1600 performs the enlargement/reduction processing for the image data in step S1302 so that the eye outlines are included as indicated by areas 1046 and 1047 in FIG. 17.

In step S1303, the eye region feature amount extraction unit 1600 performs the edge extraction processing for the image data of the left eye and the right eye, normalized in step S1102, as in step S1008. More specifically, the eye region feature amount extraction unit 1600 extracts the first-order differential edge image data in the X direction and the first-order differential edge image data in the Y direction from the normalized image data of the left eye, and extracts the first-order differential edge image data in the X direction and the first-order differential edge image data in the Y direction from the normalized image data of the right eye, to obtain a total of four pieces of edge image data. The eye region feature amount extraction unit 1600 generates a feature vector, in which the pixel value configuring the four pieces of edge image data is one element, as feature amount of the eye region of both eyes.

In step S1303, the eye region feature amount extraction unit 1600 detects the pupil motion in the horizontal direction from the border edge between the pupil and the white, and the pupil motion in the vertical direction from the border edge between the pupil and the white and from the edge of the upper eyelid. Instead of the edge, the luminance, color, frequency, and their histograms may also be used.

In step S1012, the line-of-sight estimation unit 1700 uses the feature amount corresponding to the face direction, obtained in step S1008, and the feature amounts of the right eye and the left eye, obtained in step S1011, to generate a line-of-sight feature amount.

Figure 18:
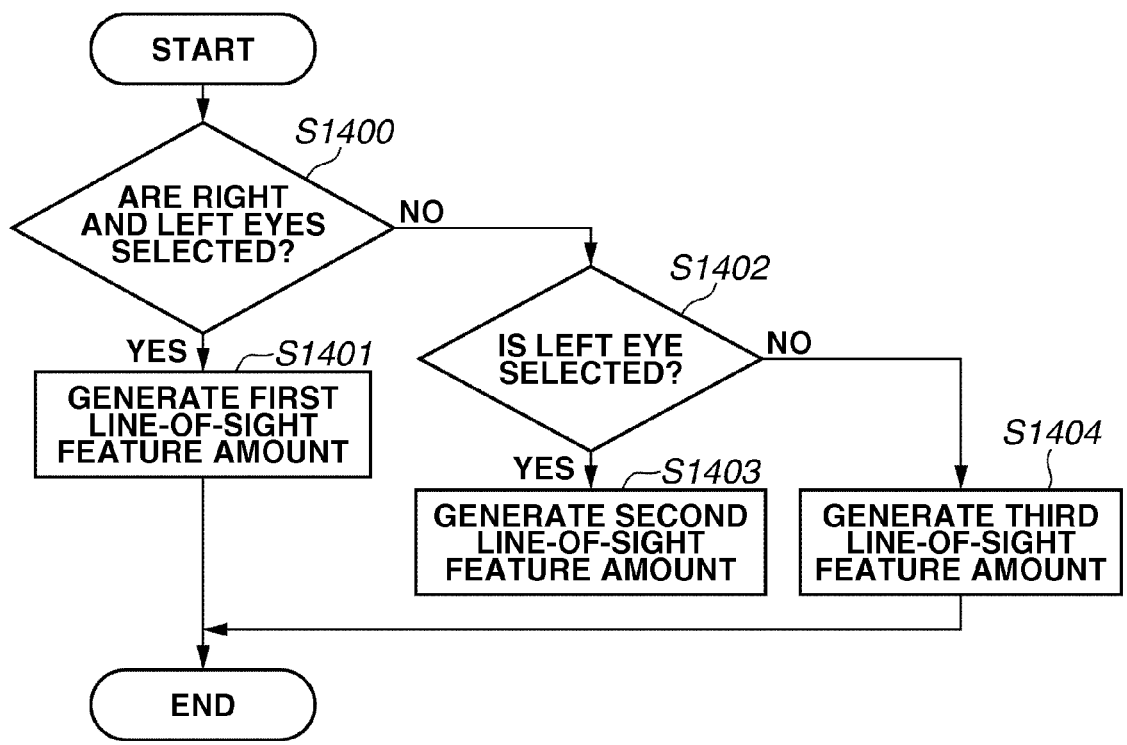
FIG. 18 is a flowchart illustrating the detailed processing procedure for generating the line-of-sight feature amount.

FIG. 18 is a flowchart illustrating the detailed processing procedure for generating the line-of-sight feature amount performed in step S1012. In step S1400, the line-of-sight estimation unit 1700 determines whether the right and left eyes are selected in step S1010. If the right and left eyes are selected, the line-of-sight estimation unit 1700 uses the feature amount corresponding to the face direction, extracted in step S1008, and the feature amount of the right eye region and the feature amount of the left eye region, extracted in step S1011, to generate the first line-of-sight feature amount in step S1401. In the present exemplary embodiment, the line-of-sight estimation unit 1700 links the feature amount corresponding to the face direction to the feature amount of the right eye region and the feature amount of the left eye region. In that case, the line-of-sight estimation unit 1700 normalizes each feature amount to the predetermined size. Alternatively, the line-of-sight estimation unit 1700 may establish a link for the right eye and the left eye separately. That is, the line-of-sight estimation unit 1700 may link the feature amount corresponding to the face direction to the feature amount of the left eye region and link the feature amount corresponding to the face direction to the feature amount of the right eye region.

On the other hand, if it is determined in step S1400 that the right and left eyes are not selected, the line-of-sight estimation unit 1700 determines in step S1402 whether the left eye is selected in step S1010. If the left eye is selected, the line-of-sight estimation unit 1700 uses the feature amount corresponding to the face direction, extracted in step S1008, and the feature amount of the left eye region, extracted in step S1011, to generate the second line-of-sight feature amount in step S1403.

On the other hand, if it is determined in step S1402 that the left eye is not selected, the line-of-sight estimation unit 1700 uses the feature amount corresponding to the face direction, extracted in step S1008, and the feature amount of the right eye region, extracted in step S1011, to generate the third line-of-sight feature amount in step S1404.

Figure 19:
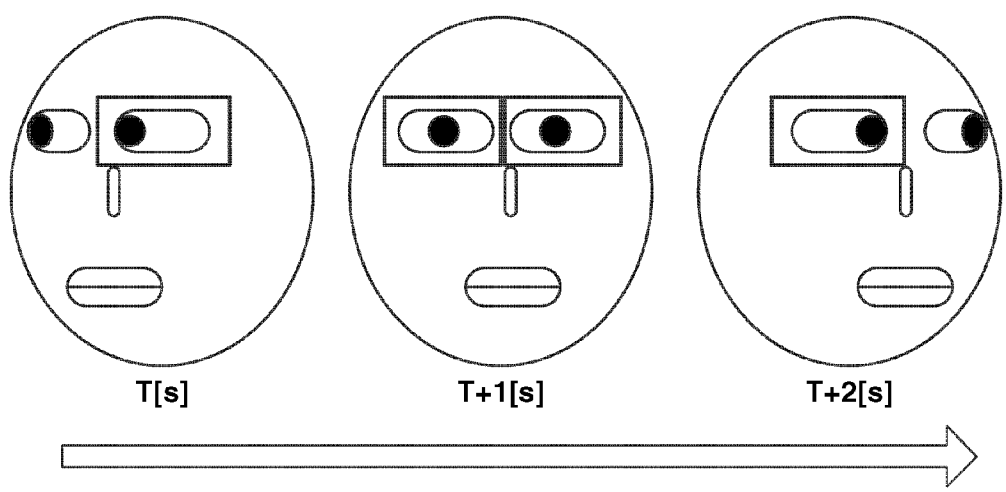
FIG. 19 is a diagram illustrating the generation method of the line-of-sight feature amount.

As described above, the line-of-sight estimation unit 1700 generates in step S1012 the line-of-sight feature amount based on the selection result selected in step S1010. For example, in T[s] where the face direction is the right direction and, therefore, the visibility of the right eye is low as illustrated in FIG. 19, the line-of-sight estimation unit 1700 uses the feature amount corresponding to the face direction and the feature amount of the left eye region to generate the second line-of-sight feature amount. In T+1[s] where the face direction is the front direction and, therefore, both the left eye and the right eye are well visible, the line-of-sight estimation unit 1700 uses the feature amount corresponding to the face direction and the feature amounts of the right eye region and the left eye region to generate the first line-of-sight feature amount. In T+2[s] where the face direction is the left direction and, therefore, the visibility of the left eye is low, the line-of-sight estimation unit 1700 uses the feature amount corresponding to the face direction and the feature amount of the right eye region to generate the third line-of-sight feature amount.

The SVM that estimates line-of-sight direction learns in advance the positive line-of-sight feature amount corresponding to a case when the line of sight is in the direction of the camera and the negative line-of-sight feature amount corresponding to a case when the line of sight is not in the direction of the camera. In step S1013, the line-of-sight estimation unit 1700 uses the SVM to generate an identification model corresponding to the line-of-sight feature amount generated in step S1012 and, based on the generated identification model, estimates whether the line of sight is in the direction of the camera. Although the SVM is used as the classifier for estimating the line of sight in the present exemplary embodiment, the classifier is not limited to the SVM.

In the present exemplary embodiment, whether the line of sight is in the direction of the camera is determined as one of two values. However, by providing a plurality of classifiers each of which detects a specific direction, it is also possible to detect a direction to which the line of sight is directed.

As described above, the feature amount of one of the right-eye region, left-eye region, and both-eye region is selected in the present exemplary embodiment based on the evaluation value of the line of sight to generate the line-of-sight feature amount. This configuration allows the line of sight to be detected accurately without significantly reducing the line-of-sight detection accuracy even when the face turns sideways and one of the eyes is hidden or when the eyes are hidden by hair.

In the present exemplary embodiment, the eye region is selected based on the visibility of the left eye and the right eye, and the feature amount is extracted only for the selected eye region to reduce the processing load as much as possible. It is also possible to always prepare a plurality of feature amounts. That is, the line-of-sight estimation unit 1700 always extracts a plurality of feature amounts in step S1013, for example, the feature amount corresponding to the face direction and the feature amount of the left eye region, the feature amount corresponding to the face direction and the feature amount of the right eye region, and the feature amount corresponding to the face direction and the feature amount of the both-eye region. By doing so, when estimating the line-of-sight direction later, the line-of-sight estimation unit 1700 may select one of a plurality of feature amounts based on the line-of-sight evaluation value.

In addition, the line-of-sight estimation unit 1700 may estimate a plurality of line-of-sight directions for a plurality of feature amounts and, based on the line-of-sight evaluation value, select a line-of-sight direction from a plurality of estimation results of the line-of-sight direction.

Next, a second exemplary embodiment of the present invention will be described. The present exemplary embodiment relates to an imaging apparatus, such as a digital camera, that automatically releases the shutter when the line of sight of the object turns in the direction of the imaging apparatus.

Figure 20:
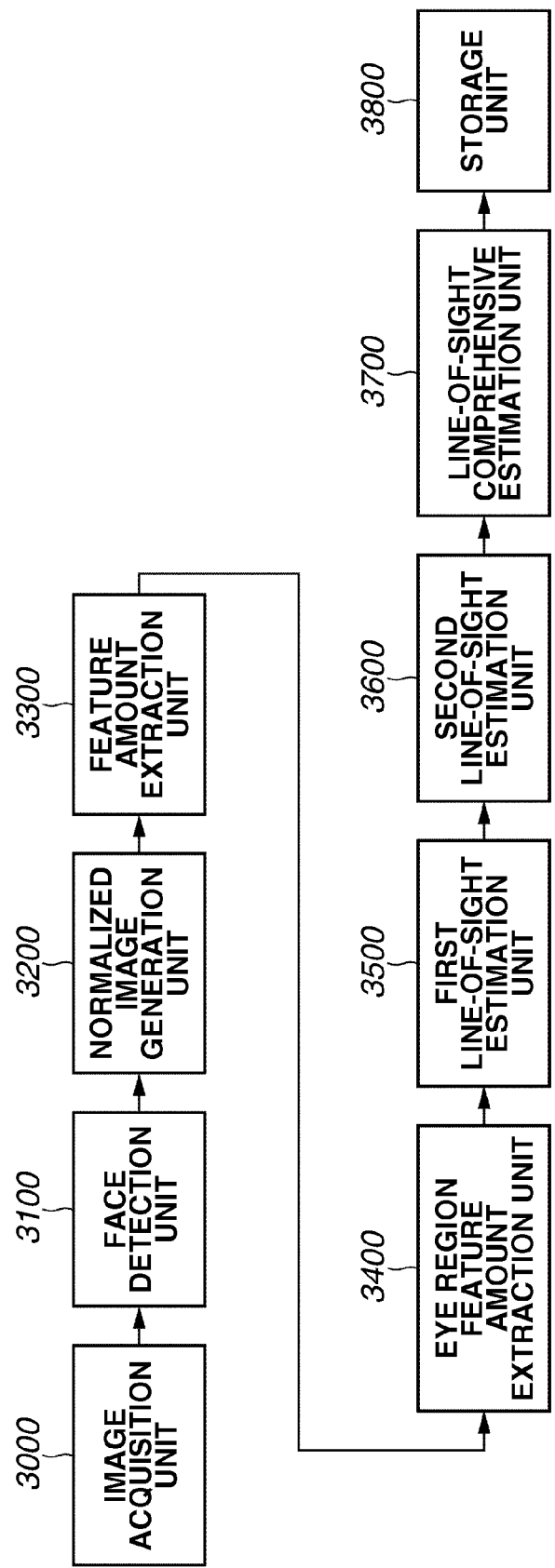
FIG. 20 is a diagram illustrating the functional configuration of a line-of-sight detection apparatus in a second exemplary embodiment of the present invention.

FIG. 20 is a diagram illustrating the functional configuration of a line-of-sight detection apparatus in the second exemplary embodiment. The functional configuration illustrated in FIG. 20 is the configuration implemented by downloading the line-of-sight detection program of the present exemplary embodiment into the memory of a personal computer (PC) for execution by the CPU.

As illustrated in FIG. 20, the line-of-sight detection apparatus in the present exemplary embodiment includes an image acquisition unit 3000, a face detection unit 3100, a normalized image generation unit 3200, a feature amount extraction unit 3300, an eye region feature amount extraction unit 3400, a first line-of-sight estimation unit 3500, a second line-of-sight estimation unit 3600, a line-of-sight comprehensive estimation unit 3700, and a storage unit 3800.

The image acquisition unit 3000 acquires image data. The face detection unit 3100 detects the position of the face, the feature points of the outer corner and the inner corner of the eye and so on, and the pupil from the image data acquired by the image acquisition unit 3000. The normalized image generation unit 3200 uses the feature point positions of face, detected by the face detection unit 3100, to normalize the image data so that the face size is the predetermined size and the face is in the upright direction. The feature amount extraction unit 3300 uses the normalized image data, generated by the normalized image generation unit 3200, to extract the feature amount corresponding to the face direction. The eye region feature amount extraction unit 3400 uses the normalized image data, generated by the normalized image generation unit 3200, to extract the feature amount of the left eye region and the feature amount of the right eye region.

The first line-of-sight estimation unit 3500 uses the feature amount corresponding to the face direction, extracted by the feature amount extraction unit 3300, and the feature amount of the left eye region, extracted by the eye region feature amount extraction unit 3400, to perform the first line-of-sight estimation. The second line-of-sight estimation unit 3600 uses the feature amount corresponding to the face direction, extracted by the feature amount extraction unit 3300, and the feature amount of the right eye region, extracted by the eye region feature amount extraction unit 3400, to perform the second line-of-sight estimation. The line-of-sight comprehensive estimation unit 3700 performs the comprehensive line-of-sight estimation based on the result of the first line-of-sight estimation and the second line-of-sight estimation. The storage unit 3800 stores the image data, acquired by the image acquisition unit 3000, into a memory, such as the nonvolatile memory, based on the line-of-sight comprehensive estimation result.

Figure 21:
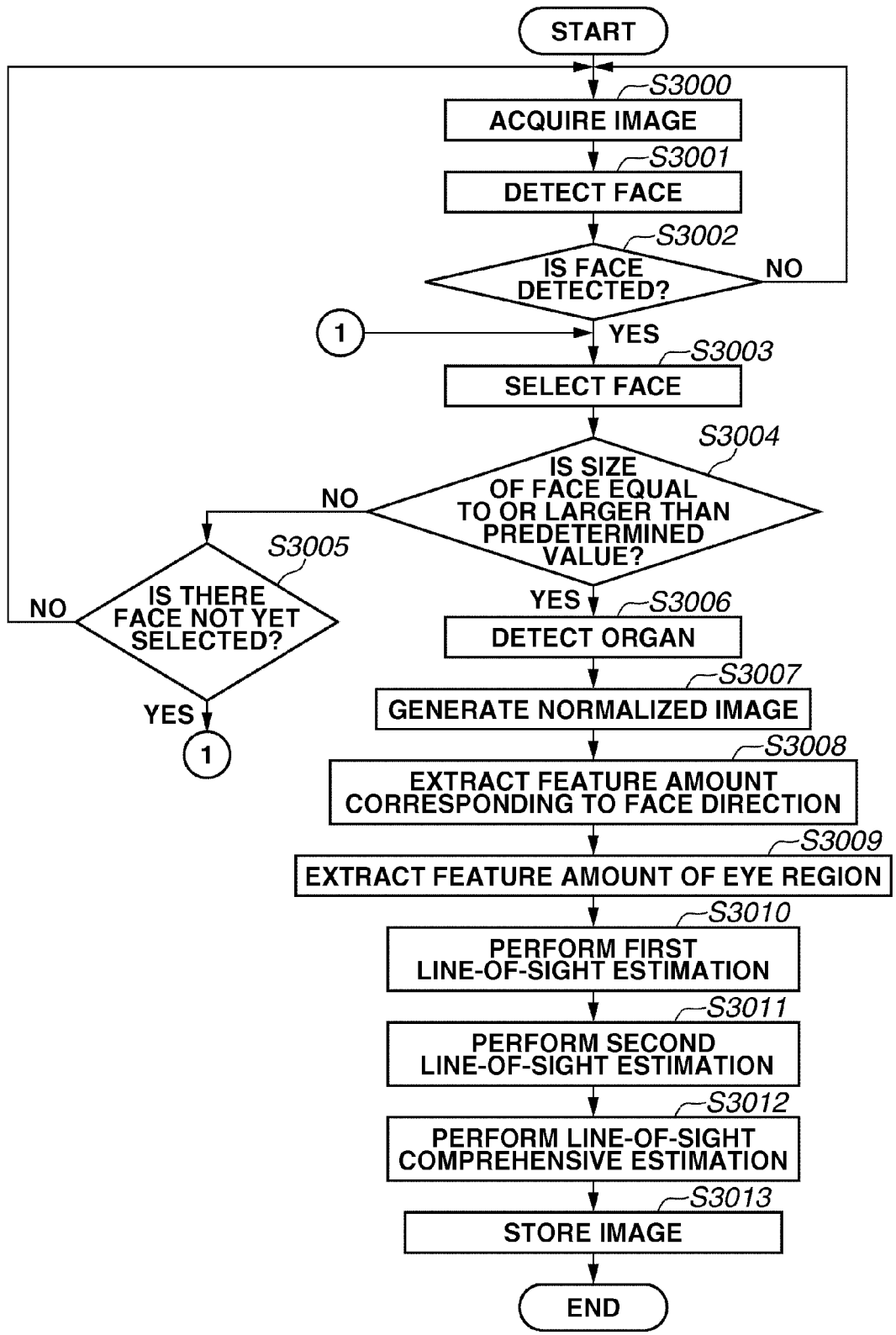
FIG. 21 is a flowchart illustrating a line-of-sight detection method in the second exemplary embodiment of the present invention.

FIG. 21 is a flowchart illustrating a line-of-sight detection method in the second exemplary embodiment. The following describes the line-of-sight detection method in the present exemplary embodiment with reference to FIG. 21. Step S3000 to step S3008 are similar to step S1000 to step S1008 in FIG. 2 and, therefore, the description is not repeated here.

In step S3009, the eye region feature amount extraction unit 3400 uses the normalized image data, which is one of the two types of normalized image data generated in step S3007 and has a higher resolution, to extract the feature amount of the left eye region and the feature amount of the right eye region. In step S3010, the first line-of-sight estimation unit 3500 uses the feature amount corresponding to the face direction, extracted in step S3008, and the feature amount of the left eye region, extracted in step S3009, to perform the first line-of-sight estimation. In step S3011, the second line-of-sight estimation unit 3600 uses the feature amount corresponding to the face direction, extracted in step S3008, and the feature amount of the right eye region, extracted in step S3009, to perform the second line-of-sight estimation. For the line-of-sight estimations, the SVM is used as in the first exemplary embodiment. Note that the line-of-sight estimation method is not limited to the method described above.

In step S3010 and step S3011, the first line-of-sight estimation unit 3500 and the second line-of-sight estimation unit 3600 may output, as the first line-of-sight estimation result and the second line-of-sight estimation result, a binary value which indicates whether each of the first line-of-sight and the second line-of-sight is directed in the predetermined direction, respectively. The values output from the first line-of-sight estimation unit 3500 and the second line-of-sight estimation unit 3600 may indicate the direction of the first line-of-sight and the direction of the second line-of-sight. In step S3012, the line-of-sight comprehensive estimation unit 3700 comprehensively determines the line-of-sight direction based on the first line-of-sight estimation result and the second line-of-sight estimation result.

Figure 22:
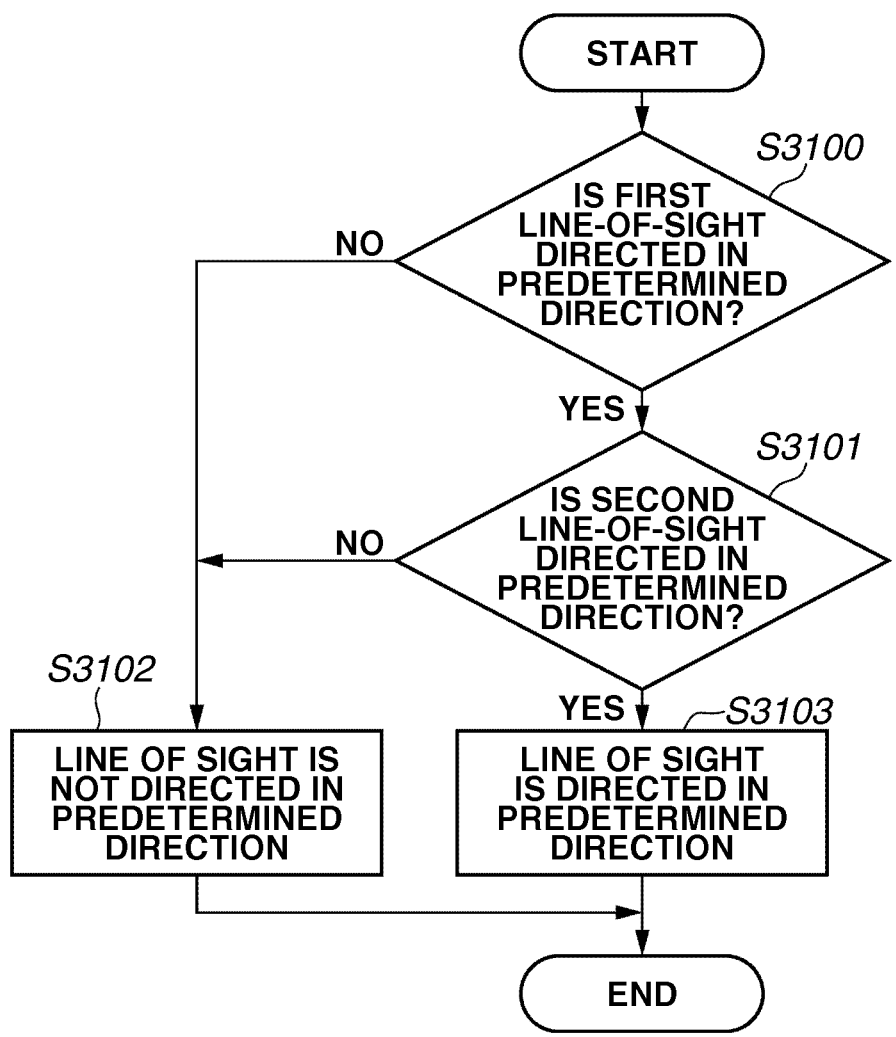
FIG. 22 is a flowchart illustrating the detailed processing procedure for determining the line-of-sight direction comprehensively.

FIG. 22 is a flowchart illustrating the detailed processing procedure for comprehensively determining the line-of-sight direction in step S3012 in FIG. 21. In step S3100, the line-of-sight comprehensive estimation unit 3700 determines whether the first line-of-sight is directed in the predetermined direction based on the first line-of-sight estimation result. If the first line-of-sight is directed in the predetermined direction, the line-of-sight comprehensive estimation unit 3700 confirms in step S3101 whether the second line-of-sight is directed in the predetermined direction based on the second line-of-sight estimation result. If the second line-of-sight is directed in the predetermined direction, the line-of-sight comprehensive estimation unit 3700 determines in step S3103 that the line of sight is directed in the predetermined direction.

On the other hand, if it is determined in step S3100 that the first line-of-sight is not directed in the predetermined direction or if it is determined in step S3101 that the second line-of-sight is not directed in the predetermined direction, the processing proceeds to step S3102. In step S3102, the line-of-sight comprehensive estimation unit 3700 determines that the line of sight is not directed in the predetermined direction.

That is, only if both the first line-of-sight, determined by the feature amount of the left eye region and the feature amount corresponding to the face direction, and the second line-of-sight, determined by the feature amount of the right eye region and the feature amount corresponding to the face direction, are directed in the predetermined direction, the line-of-sight comprehensive estimation unit 3700 determines that the line of sight is directed in the predetermined direction. Note that the line of sight determination method is not limited to this method. It is also possible to determine that the line of sight is directed in the predetermined direction if one of the first line-of-sight and the second line-of-sight is directed in the predetermined direction.

Figure 23:
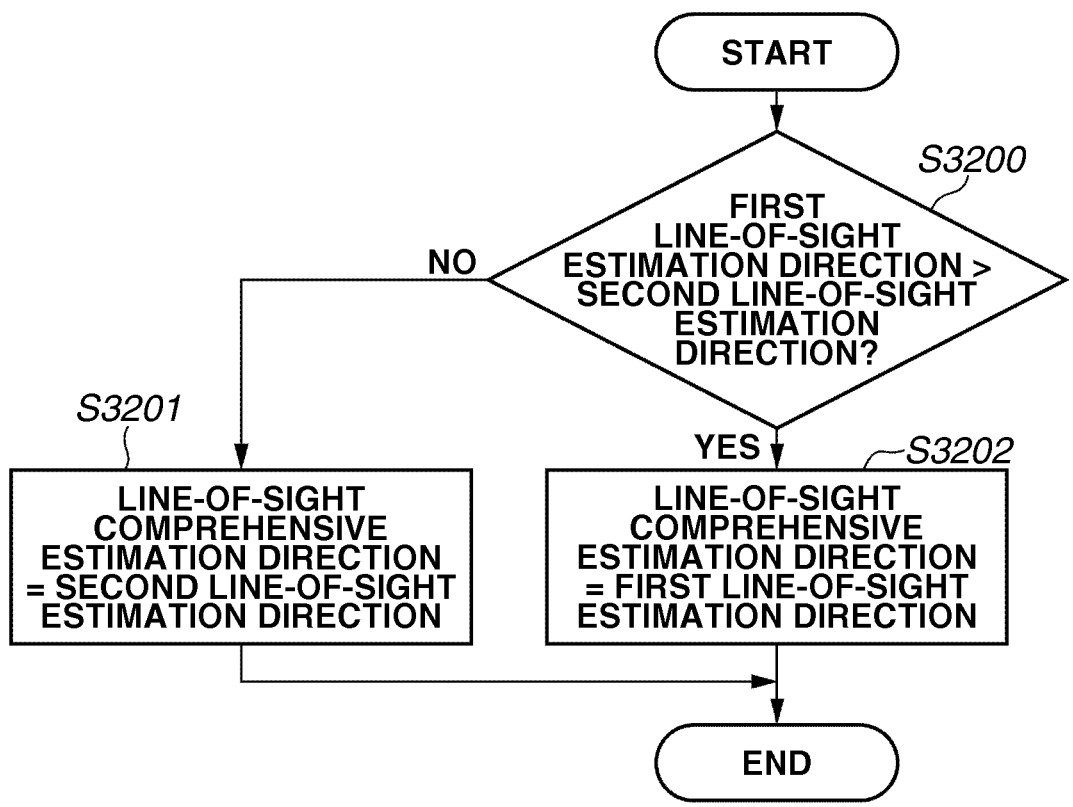
FIG. 23 is a flowchart illustrating the line-of-sight comprehensive estimation-value determination method when the line-of-sight estimation result is a direction.
Figure 24:
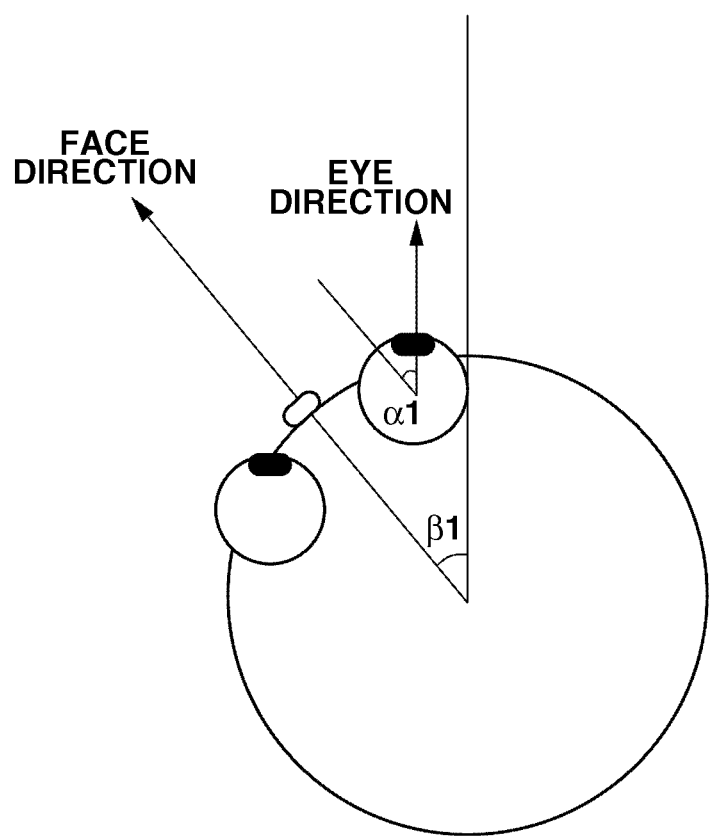
FIG. 24 is a diagram illustrating the relation between the face direction and the eye direction.

The processing has been described in which the output of the line-of-sight estimation result in step S3010 and step S3011 is a binary value indicating whether the line of sight is directed in the predetermined direction. Referring to FIG. 23, the following describes the line-of-sight comprehensive estimation value determination method in which the output value of the line-of-sight estimation result in step S3010 and step S3011 is the direction itself. In the description below, the first line-of-sight estimation result obtained in step S3010 is referred to as the first line-of-sight estimation value, and the second line-of-sight estimation result obtained in step S3011 as the second line-of-sight estimation value.

In step S3200, the line-of-sight comprehensive estimation unit 3700 compares the first line-of-sight estimation value and the second line-of-sight estimation value. If the first line-of-sight estimation value is larger than the second line-of-sight estimation value, the line-of-sight comprehensive estimation unit 3700 uses the first line-of-sight estimation value as the line-of-sight comprehensive estimation value in step S3202. On the other hand, if it is determined in step S3200 that the first line-of-sight estimation value is equal to or smaller than the second line-of-sight estimation value, the line-of-sight comprehensive estimation unit 3700 uses the second line-of-sight estimation value as the line-of-sight comprehensive estimation value in step S3201.

As the method for integrating the first line-of-sight estimation value and the second line-of-sight estimation value, the method has been described in which the larger of the two line-of-sight estimation values is set as the line-of-sight comprehensive estimation value. In addition to this method, there is another method for integrating the first line-of-sight estimation value and the second line-of-sight estimation value. In another method, the average of the line-of-sight estimation values is set as the line-of-sight comprehensive estimation value. In still another method, the first line-of-sight reliability and the second line-of-sight reliability are calculated as in the first exemplary embodiment. The calculated reliability is used as the weight for the first line-of-sight estimation value and the second line-of-sight estimation value as indicated in the expression given below.

Line-of-sight comprehensive estimation value=First line-of-sight reliability×First line-of-sight estimation value+Second line-of-sight reliability×Second line-of-sight estimation value In step S3013, the storage unit 3800 stores the image data, acquired in step S3000, into the memory such as a nonvolatile memory if the line-of-sight comprehensive estimation result indicates that the line of sight is directed in the direction of the imaging apparatus. This allows imaging to be performed when the line of sight of a person, who is the object, is directed in the direction of the imaging apparatus. As described above, the method in the present exemplary embodiment calculates the first line-of-sight, determined by the feature amount of the left eye region and the feature amount corresponding to the face direction, and the second line-of-sight, determined by the feature amount of the right eye region and the feature amount corresponding to the face direction, separately and estimates the line of sight direction comprehensively. This estimation method used in the present exemplary embodiment addresses the problem of a dominant eye and increases the line-of-sight estimation accuracy.

The present invention may also be implemented by performing the following processing. That is, the software (program) for implementing the function of the above-described exemplary embodiments is supplied to a system or an apparatus via a network or various storage media to allow the computer (CPU or microprocessor unit (MPU)) of the system or the apparatus to read the program for execution.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-174730 filed Aug. 3, 2010, which is hereby incorporated by reference herein in its entirety.

What is claimed is:

1. A line-of-sight detection apparatus comprising:
   a detection unit configured to detect a face from image data;
   a first extraction unit configured to extract a feature amount corresponding to a direction of the face from the image data;
   a calculation unit configured to calculate a line-of-sight reliability of each of a right eye and a left eye based on the face;
   a selection unit configured to select at least one eye of which the calculated line-of-sight reliability is higher than a threshold for each eye, from the right eye and the left eye;
   a second extraction unit configured to extract a feature amount of an eye region of the selected eye from the image data; and
   an estimation unit configured to estimate a line of sight of the face based on the feature amount corresponding to the face direction and the feature amount of the eye region of the selected eye;
   a generation unit configured to generate a low resolution face image and a high-resolution face image from the detected face, wherein the first extraction unit is configured to extract a feature amount corresponding to a direction of the face from the low-resolution face image, and a second extraction unit configured to extract a feature amount of an eye region of the selected eye from the high-resolution face image.

2. The line-of-sight detection apparatus according to claim 1, wherein the calculation unit calculates the line-of-sight reliability as a binary value representing whether the line of sight is reliable.

3. The line-of-sight detection apparatus according to claim 1, wherein the calculation unit calculates the line-of-sight reliability based on a spatial arrangement relation of organs of the face.

4. The line-of-sight detection apparatus according to claim 1, wherein the calculation unit calculates the line-of-sight reliability based on a distribution of organs of the face.

5. The line-of-sight detection apparatus according to claim 1, wherein the calculation unit calculates the line-of-sight reliability based on a size of an eye or a pupil of the face.

6. The line-of-sight detection apparatus according to claim 1, wherein the calculation unit calculates the line-of-sight reliability based on the feature amount corresponding to the face direction extracted by the first extraction unit.

7. The line-of-sight detection apparatus according to claim 1, wherein the feature amount is at least one of an edge, luminance, color, frequency, and histogram thereof.

8. A line-of-sight detection method comprising:
   detecting a face from image data;
   extracting a feature amount corresponding to a direction of the face from the image data;
   calculating a line-of-sight reliability of each of a right eye and a left eye based on the face;
   selecting at least one eye of which the calculated line-of-sight reliability is higher than a threshold for each eye, from the right eye and the left eye;
   extracting a feature amount of an eye region of the selected eye from the image data; and
   estimating a line of sight of the face based on the feature amount corresponding to the face direction and the feature amount of the eye region of the selected eye;
   a generation unit configured to generate a low resolution face image and a high-resolution face image from the detected face, wherein the first extraction unit is configured to extract a feature amount corresponding to a direction of the face from the low-resolution face image, and a second extraction unit configured to extract a feature amount of an eye region of the selected eye from the high-resolution face image.

9. A non-transitory computer readable storage medium storing a program that causes a computer to execute the line-of-sight detection method according to claim 8.

* * * * *